(12) United States Patent
Varel

(10) Patent No.: US 6,902,726 B1
(45) Date of Patent: Jun. 7, 2005

US006902726B1

(54) REDUCTION OF ODOR GASES FROM WASTE USING PLANT-DERIVED OILS

(75) Inventor: Vincent H. Varel, Hastings, NE (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 149 days.

(21) Appl. No.: 10/227,727

(22) Filed: Aug. 26, 2002

Related U.S. Application Data

(60) Provisional application No. 60/315,618, filed on Aug. 29, 2001.

(51) Int. Cl.$^7$ .......................... A61L 11/00; B09B 3/00; C07G 17/00; C12N 1/00
(52) U.S. Cl. ................... 424/76.6; 435/262.5; 435/267; 435/801
(58) Field of Search .............................. 424/76.6, 93.1; 435/262.5, 267, 801, 243, 262

(56) References Cited

U.S. PATENT DOCUMENTS

| | | | |
|---|---|---|---|
| 3,492,223 A | * | 1/1970 | Walles ........................ 210/692 |
| 4,840,792 A | | 6/1989 | Joulain et al. |
| 5,186,722 A | * | 2/1993 | Cantrell et al. ............... 44/605 |
| 6,004,569 A | | 12/1999 | Bessette et al. |

OTHER PUBLICATIONS

Ben Hardin, Plant Oils Help Abate Livestock Odors, USDA Agricultural Research Service, www.ars.usda.gov/is/pr/2000/000912.htm, 2 pages.
Roman L. Hruska, Odors from Cattle Feedlots May One Day be Abated by Some Essential Oils–Chemicals Like Those Produced by Some Aromatic Plants, Soil, Water and Air Quality Research, ARS Quarterly Report, Jul.–Sep. 2000, www.ars.usda.gov/is/qtr/q3000/swa300.htm, 1 page.
Vincent H. Varel et al., Effect of Antimicrobial Agents on Livestock Waste Emissions, Current Microbiology vol. 40 (2000), pp. 392–397.
Vincent H. Varel et al., Plant–Derived Oils Reduce Pathogens and Gaseous Emissions from Stored Cattle Waste, Applied and Environmental Microbiology, Mar. 2001, pp. 1366–1370.
A. Ultee et al., Mechanisms of Action of Carvacrol on the Food–Borne Pathogen *Bacillus cereus,* Applied and Environmental Microbiology, Oct. 1999, pp. 4606–4610.
A. Ultee et al., Bactericidal Activity of Carvacrol Towards the Food–Borne Pathogen *Bacillus cereus,* Journal of Applied Microbiology, 1998, 85, 211–218.
K.A. Hammer et al., Antimicrobial Activity of Essential Oils and Other Plant Extracts, Journal of Applied Microbiology 1999, 86, 985–990.
I.E. Pol et al., Combined Action of Nisin and Carvacrol on *Bacillus cereus* and *Listeria monocytogenes,* Letters in Applied Microbiology 1999, 29, 166–170.
Ilkka M. Helander et al., Characterization of the Action of Selected Essential Oil Components on Gram–Negative Bacteria, J. Agric. Food Chem. 1998, 46, pages 3590–3595.
H.J.D. Dorman et al., Antimicrobial Agents from Plants: Antibacterial Activity of Plant Volatile Oils, Journal of Applied Microbiology 2000, 88, pp. 308–316.
Vincent H. Varel et al., Conservation of Nitrogen in Cattle Feedlot Waste with Urease Inhibitors, J. Anim. Sci. 1999, 77:1162–1168.
L.R. Beuchat, Antimicrobial Properties of Spices and Their Essential Oils, Natural Antimicrobial Systems and Food Preservation. ed. Dillon, VM and Board RG. 1994, pp. 167–179.

* cited by examiner

*Primary Examiner*—David M. Naff
*Assistant Examiner*—Deborah K. Ware
(74) *Attorney, Agent, or Firm*—John D. Fado; Curtis P. Ribando; Leslie Shaw

(57) ABSTRACT

Plant-derived oils, carvacrol and thymol, when added to human or animal waste reduce the production of gas and short-chain volatile fatty acids, and the viability of total anaerobic bacteria and fecal coliforms. In an embodiment, carvacrol or thymol are combined with eugenol.

20 Claims, 15 Drawing Sheets

REDUCTION OF ODOR GASES FROM WASTE USING PLANT-DERIVED OILS

This application claims the benefit of Provisional Application No. 60/315,618, filed Aug. 29, 2001.

BACKGROUND OF THE INVENTION

1. Field of the Invention

This invention relates to the use of plant oils to reduce pathogens and gaseous emissions from animal or human waste, particularly from excreta.

2. Description of the Prior Art

Livestock production and the waste generated can pose a threat to soil, water and air quality, and to human health. Some of the more serious problems with livestock waste include nutrient enrichment of soil and water, emission of odors and greenhouse gases, as well as presence and transmission of pathogenic microorganisms [Varel, V. H. et al. (1999), *J Anim Sci* 77:1162–1168].

Odor emitted from wastes results from an incomplete anoxic degradation of the carbohydrate, protein and lipid components [Mackie, R. I. et al. (1998), *J. Anim. Sci.* 76:1331–1342; Varel, V. H. et al. (1999), supra]. This incomplete degradation results in the formation of offensive short-chain volatile fatty acids, aromatic chemicals, amines and other nitrogenous compounds, and sulfur-containing compounds. In most of the livestock production facilities, it is not possible to control the environment whereby a complete degradation of the waste to methane and carbon dioxide occurs. Conventional anoxic digesters for production of methane were popular during the 1970's and 1980's; however, economics and technical expertise to operate them have diminished their popularity [Morse, D. et al. (1996) *J. Dairy Sci.* 79:149–153]. Similarly, oxic treatment is not economically feasible and it does little for conservation of nutrients.

Odor and greenhouse gas emissions are a direct result of microbial fermentation of waste [Mackie, R. I. et al. (1998), supra]. Thus, antimicrobial chemicals may be useful additives to waste to not only control the fermentation, but also destroy the pathogens [Varel, V. H. et al. (2001), *Appl Environ Microbiol* 67:1366–1370]. Naturally-occurring antimicrobial chemicals are desirable [Beuchat L R (1994), Antimicrobial properties of spices and their essential oils, p. 167–179. In V. M. Dillon and R. G. Board (ed.), Natural antimicrobial systems and food preservation. CAB International, Wallingford, England].

It was previously reported that chlorhexidine diacetate, in combination with iodoacetate or diphenyliodonium chloride, can be used to inhibit key anoxic degradation pathways [Varel, V. H. et al. (2000) *Curr. Microbiol.* 40:392–397]. Reduction of emissions by means of naturally occurring antimicrobial chemicals such as plant-derived oils has also been suggested [Beuchat, L. R. (1994), supra; Charai, M., M. et al. (1996), *J. Essential Oil Res.* 8:657–664; Dorman, H. J. D. et al. (2000), *J. Appl. Bacteriol.* 88:308–316; Helander, I. K. et al. (1998), *J. Agric. Food Chem.* 46:3590–3595; and Ultee, A. et al. (1999), *Appl. Environ. Microbiol.* 65:4606–4610]. Numerous reports indicate that plant oils have antimicrobial activity; however, most of these studies evaluate one oil against one microorganism in an artificial medium [Dorman et al. (2000), supra]. Few studies are available which determine the effect of the oils in natural highly diverse microbial ecosystems such as those found in the gastrointestinal tract [O'gara, E. A. et al. (2000), *Appl. Environ. Microbial.* 66:2269–2273], food products [Helander, I. K. et al. (1998), supra; Kim, J. M. et al. (1995), *J. Food Sci.* 60:1364–1374; and Skandamis, P. N. et al. (2000), *Appl. Environ. Microbiol.* 66:1646–1653] or waste management systems.

Numerous studies show that carvacrol and thymol are bactericidal to pathogens [Hammer, K. A. et al. (1999), *J. Appl. Microbiol.* 86:985–990; Kim, J. M. et al. (1995), *J. Food Sci.* 60:1364–1374; Pol, I. E. et al. (1999), *Lett. Appl. Microbiol.* 29:166–170; Ultee, A. et al. (1998), *J. Appl. Microbiol.* 85:211–218; and Ultee, A. et al. (1999), *Appl. Environ. Microbiol.* 65:4606–4610] and in particular to *E. coli* O157:H7 [Helander, I. K. (1998), supra); Kim, J. M. et al. (1995), *J. Agric. Food Chem.* 43:2839–2845; and Skandamis et al., supra] in pure culture. Helander et al. (supra) have shown that the minimum inhibitory concentration with carvacrol or thymol in a pure culture system is 3 mM and 1 mM for *E. coli* O157:H7 and *Salmonella typhimurium*, respectively. Kim et al. (supra) also found that 500 µg/ml (3.3 mM) of carvacrol will kill *E. coli* O157:H7. Also, previous studies have suggested that a combination of both thymol and carvacrol oils would provide better antimicrobial action, rather than a higher content of carvacrol or thymol alone [Manou, I. et al. (1998), *J. Appl. Microbiol.* 84:368–376; Paster, N. et al. (1995), *J. Food Protect.* 58:81–85].

SUMMARY OF THE INVENTION

We have now discovered that the plant-derived oils, carvacrol and thymol, have the ability to reduce the production of gas and short-chain volatile fatty acids, and the viability of total anaerobic bacteria and fecal coliforms in human and animal excreta. At appropriate levels, these oils are effective when used alone or in combination with one another. We have also discovered that when eugenol is used in combination with one or both of these oils, it has the added effect of promoting lactic acid accumulation; thereby more quickly inhibiting fermentation by the anaerobic bacteria.

In accordance with this discovery, it is an object of this invention to provide a treatment for reducing odor emissions and disease emanating from human and animal waste.

It is another object of the invention to completely inhibit or reduce the production of specific compounds associated with offensive odors in human and animal waste.

It is a further object of this invention to reduce the growth and spread of pathogenic organisms associated with excreta.

It is also an object of the invention to control odor emissions and pathogens in excreted waste using naturally-occurring, plant-derived chemicals that are safe to the environment.

Another object of the invention is to reduce the generation of global warming gases from accumulated livestock waste.

Yet another object of the invention is provide a potential source of safe fertilizer for producing crops and produce that are less likely to carry food-borne pathogens than crops or produce obtained from land fertilized with untreated livestock waste.

Other objects and advantages of this invention will become readily apparent from the ensuing description.

DETAILED DESCRIPTION

Figure 1A:
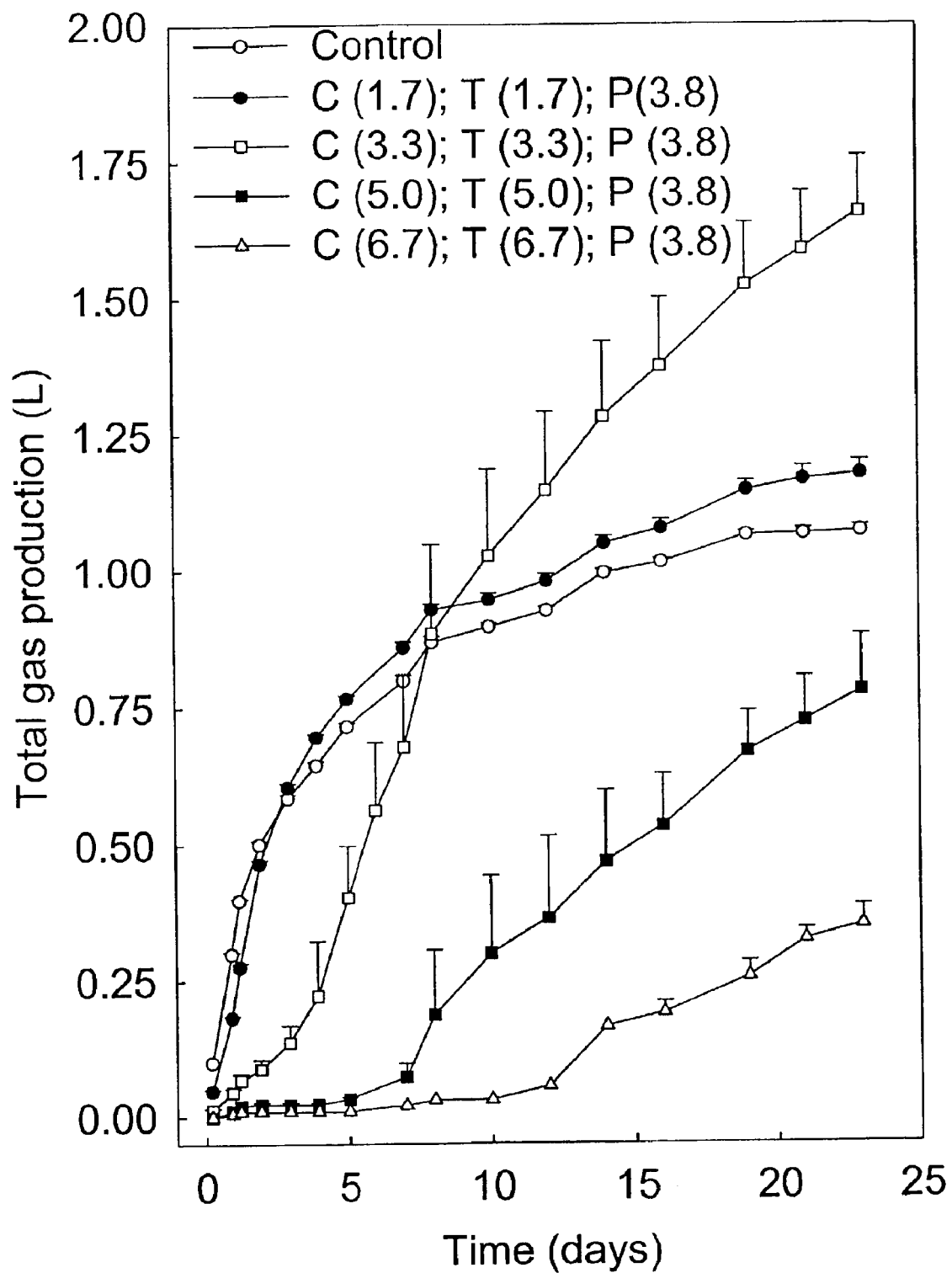
FIG. 1A is a graph showing the effect of various concentrations of carvacrol (C), thymol (T), and α-pinene (P) on total gas production of stored cattle waste in anoxic flasks.
Figure 1B:
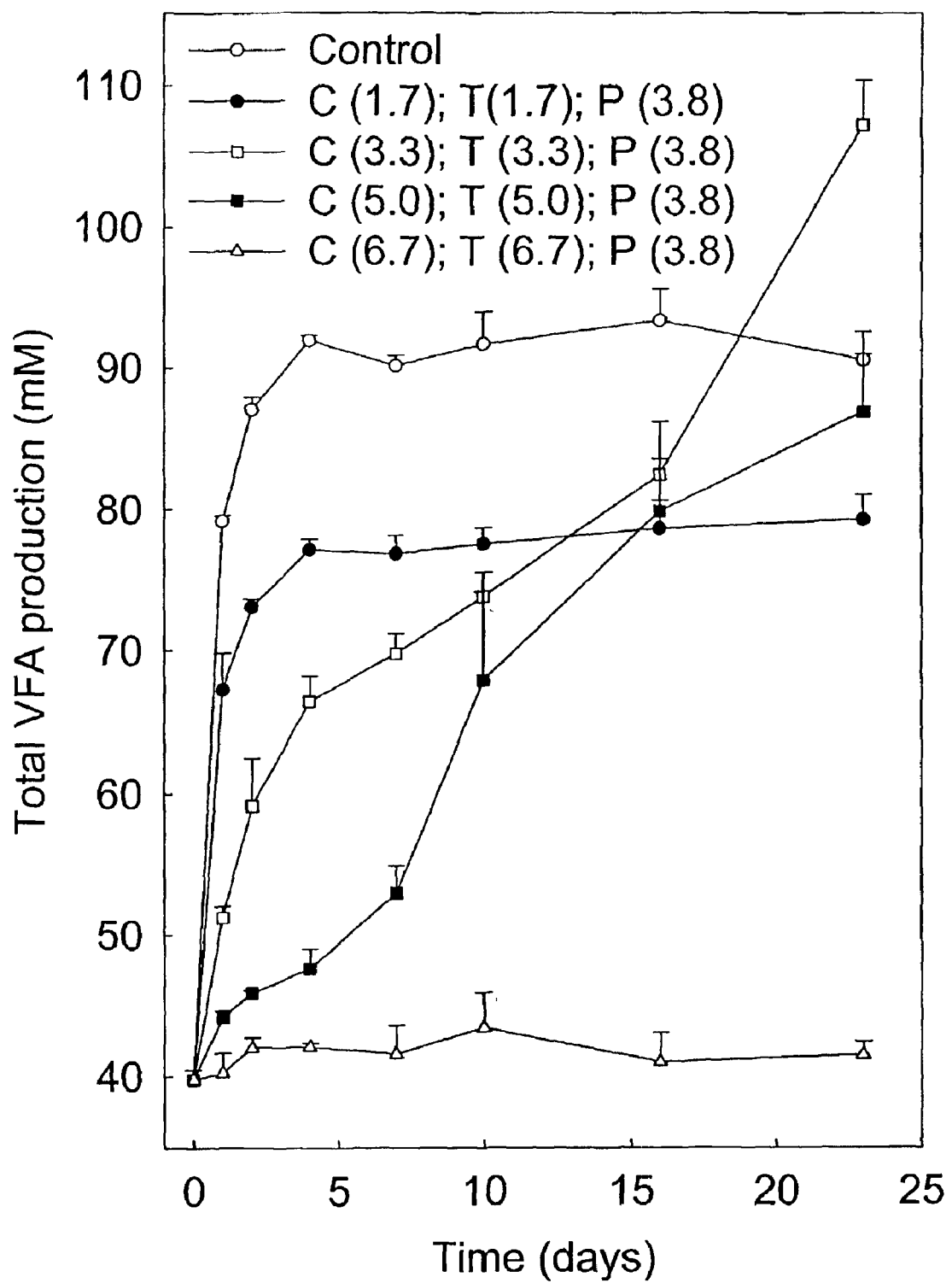
FIG. 1B is a graph showing the effect of various concentrations of carvacrol (C), thymol (T), and α-pinene (P) on total volatile fatty acid production in stored cattle waste in anoxic flasks.

The expression "an effective amount" or "suppressive amount" is used herein in reference to that quantity of carvacrol and/or thymol treatment that is necessary to obtain a significant reduction in either the level of fermentative production of gaseous emissions from waste material or in the pathogen level relative to that occurring in an untreated control under suitable conditions of treatment as described herein. The minimum rate of application of these odor suppressive agents, whether alone or in combination, should be on the order of about 10 mM, and preferably 13 mM. In a preferred embodiment of the invention, carvacrol and thymol are added in approximately equal molar amounts. In the most preferred embodiment of the invention, the combined level of carvacrol and thymol will be at least about 13.3 mM; for example 6.7 mM carvacrol and 6.7 mM thymol, or 13.3 mM of either carvacrol or thymol. What constitutes an effective amount of these agents is in part determined by the particular type of waste being treated. The examples show that in cattle waste, 13.3 mM carvacrol or thymol suppressed essentially all fermentation activity in a waste slurry of feces, urine and water (50:35:15). However, with swine waste at this same ratio, 16.75 mM was required to suppress most fermentation activity. The maximum levels of these agents for purposes of the invention would be limited by economics. It is envisioned that the maximum combined level would be on the order of about 50 mM.

Carvacrol oil and thymol oil (thyme oil) are readily isolated from plants, such as *Monarda* sp., by conventional extraction and distillation methods. Alternatively, these compounds may be produced by synthetic means as well-known in the art. Carvacrol is liquid at room temperature; whereas thymol is crystalline and has a melting point of 51.5° C. Optionally, the odor-suppressive agents may be combined with a liquid or solid carrier prior to application to the waste. Suitable solid carriers include sand, calcium oxide, calcium carbonate, vermiculite, corn cops, starch, flour, ground newsprint, diatomaceous earth and the like. Liquid carriers could be nonpolar solvents, such as oils or other lipids, ether, hydrocarbons, etc., or even certain polar solvents, such as ethanol and other common alcohols. The agents could also be dispersed in water or other non-miscible vehicle by means of an emulsifier or other suspending agent. Melts, solutions and dispersions of these agents can be easily applied to the target substrate in any conventional manner such as by spraying, injecting, or fumigating.

The agents of this invention may also be combined with odor-masking agents, such as α-pinene, that do not contribute significantly to control of pathogenic organisms in the waste or to reduction of gaseous emissions. Of course, the carvacrol and thymol may also be combined with other active chemical agents, such as eugenol, or with nonpathogenic organisms that would be useful in either digesting the waste or in suppressing populations of undesirable microorganisms.

This invention finds utility for treating various forms of human and animal waste, particularly excreta, to include urine and fecal material, but also other wastes, such as spilled feed occurring in feedlots. The invention is envisioned for use with excretal waste from herbivores, carnivores and omnivores, but especially from herbivores. Exemplary waste is from livestock such as from cattle and swine, but also from other animals, such as sheep, rabbits, bison, horses and poultry and exotic animals (e.g. zoo animals) that may have a similar organic matter content, particularly in regards to the protein, fat and lipid constitution. The invention also finds application for treating: human waste that may accumulate in recreation vehicles, pit toilets, portable toilets, etc.; waste from domestic pets (e.g. cats and dogs) that may accumulate in litter boxes, cages and yards; waste that accumulates in animal confinement areas, such as in pens, animal production areas, zoos and pet shelters; waste that is dropped in the field; and waste in storage areas such as manure piles and treatment lagoons.

When applied to waste in an effective amount, carvacrol and thymol inhibit most fermentation activity and the pH of the waste remains approximately neutral (6.5 to 7.0). The neutral pH keeps the short-chain acids in the ionized, less volatile state, and thereby reduces gaseous emissions. When eugenol is combined with the carvacrol and/or thymol as previously mentioned, the eugenol allows lactic acid to accumulate even though the production of short chain volatile fatty acids responsible for offensive odors is suppressed. Eugenol has this same effect on lactic accumulation when it is added individually to fermentable waste. The accumulation of lactic acid will rapidly lower the pH to below about 4.5, and thereby stop all production of the volatile fatty acids. Typically the eugenol will be added as a minor component (less than about 50%) relative to the carvacrol or thymol, but it may added at a higher level, such as up to about 75%, or even up to about 90%.

The following examples are intended to further illustrate the invention, without any intent for the invention to be limited to the specific embodiments described therein. All references disclosed herein are incorporated by reference.

EXAMPLE 1

The Effect of the Antimicrobial Plant Oils on Cattle Waste under Anoxic Conditions.

Waste was collected and processed in similar manner to the study described by Varel, V. H. et al. [*Curr. Microbiol.* (2000) 40:392–397]. The waste slurry was divided into 500-ml aliquots and plant oils (carvacrol, thymol and α-pinene) were added directly at the desired concentration. The slurry was blended 1 min to provide a homogenous mixing of the antimicrobial oils and poured into a 1-liter Erlenmeyer flask, which was sealed with a rubber stopper and left stationary at ambient temperature (25° C). Treatments were in triplicate, and the contents in the flasks were gently swirled before being sampled at the times indicated.

Gas volume and composition, short-chain volatile fatty acids, and L-lactate in the flasks were determined as previously described [Miller, T. L. et al., 1974, Appl. Microbiol. 27:985–987; Richardson, A. J. et al., 1989, Lett. Appl. Microbiol. 9:5–8; Varel, V. H., et al. (2000) Curr. Microbiol. 40:392–397)].

Total culturable anaerobic bacteria and fecal coliforms were enumerated from a 1 ml sample removed from each flask. The sample was serially diluted in anaerobic buffer and triplicate roll tubes from each of three dilutions, containing 30% ruminal fluid-based medium were inoculated as previously described [Varel, V. H. et al., 1989, Appl. Environ. Microbiol. 55:148–153]. Roll tubes were incubated at 35° C., and colonies were counted after 7 days. Fecal coliforms were enumerated with 3M Petrifilm® E. coli/ Coliform Count Plates (3M Microbiology Products, St. Paul, Minn.). Triplicate plates for each of three dilutions were inoculated, incubated at 35° C., and colonies were counted using the AOAC Official Methods described in literature provided with the plates. Briefly, total coliform numbers consisted of both red and blue colonies associated with gas at 24 h. All chemicals were purchased from Sigma Chemical Company (St. Louis, Mo.) with the exception of carvacrol which was obtained from Aldrich (Milwaukee, Wis). Data were analyzed as a split-plot in time with the GLM procedure of Statistical Analysis System (SAS). The results are reported in FIGS. 1A–1D and in Table 1.

Figure 1C:
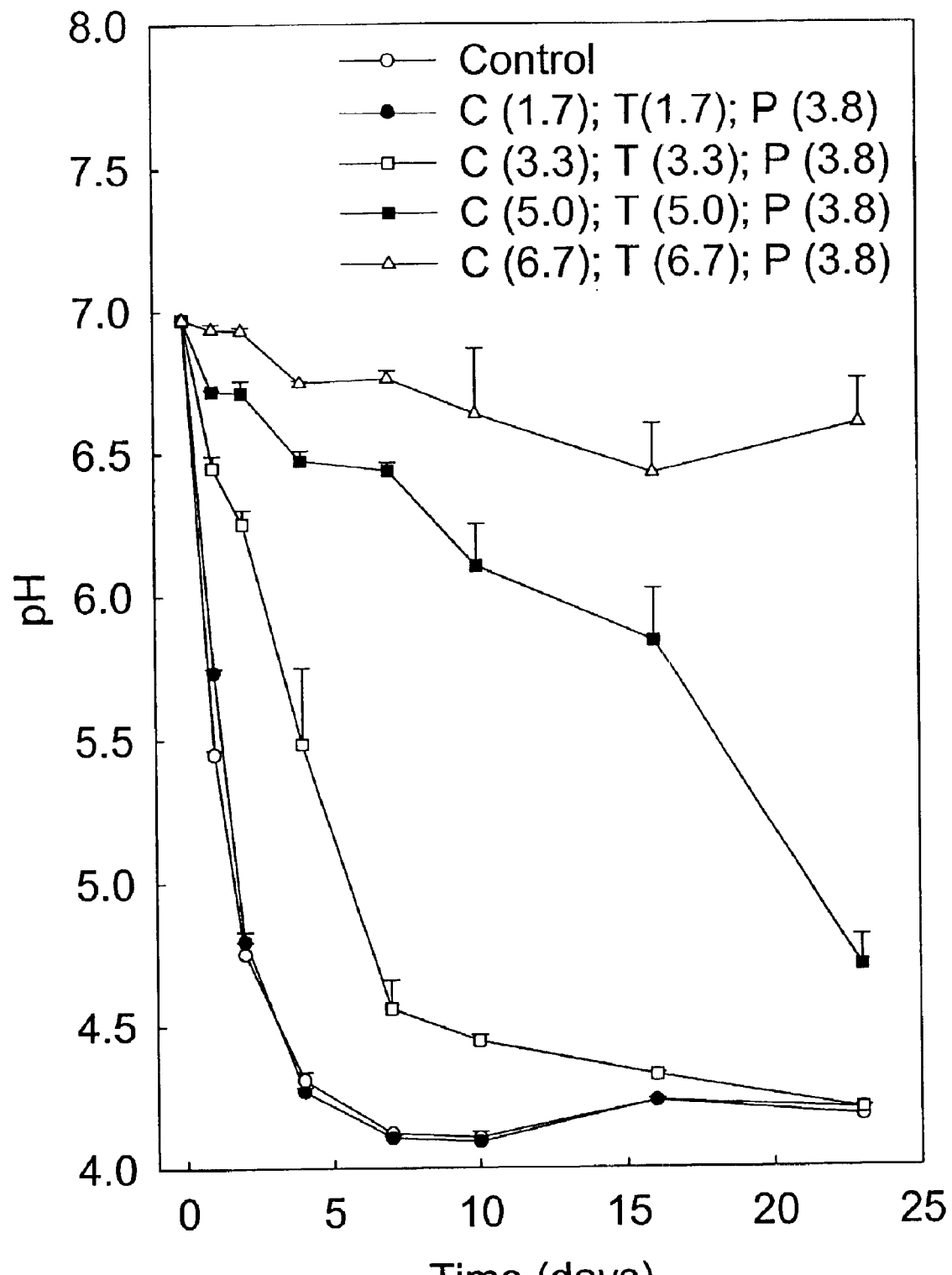
FIG. 1C is a graph showing the effect of various concentrations of carvacrol (C), thymol (T), and α-pinene (P) on pH of stored cattle waste in anoxic flasks.
Figure 1D:
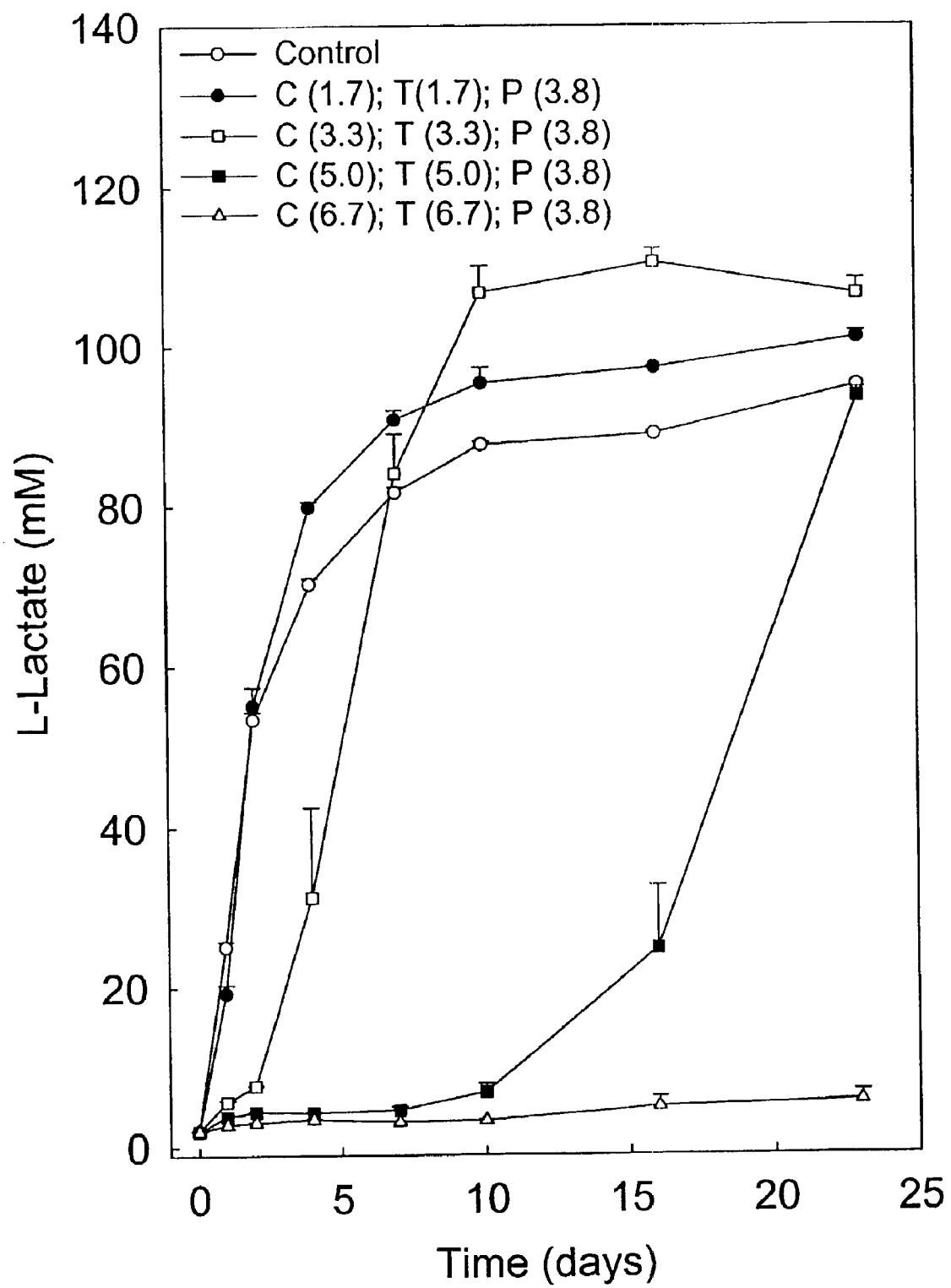
FIG. 1D is a graph showing the effect of various concentrations of carvacrol (C), thymol (T), and α-pinene (P) on L-lactate production in of stored cattle waste in anoxic flasks.

Data in FIGS. 1A–1D indicated that a combination of carvacrol and thymol at 6.7 mM each and pinene (3.8 mM) inhibited most microbial activity for 23 days in anoxic flasks containing cattle waste. After approximately 7 days, some gas production was observed at this treatment concentration (FIG. 1A); however, no increases in total volatile fatty acids (FIG. 1B) or lactate (FIG. 1D) were observed. The pH data also supported an inhibition of acid production or fermentation activity because it remained between 6.5 and 7 (FIG. 1C). The gas that was produced most likely was $CO_2$ (not analyzed), because no $CH_4$ and only traces of $H_2$ were detected. The treatment, 3.3 mM each of carvacrol and thymol with 3.8 mM pinene, suggests that several metabolic groups of microorganisms may be inhibited, which in turn allows others to flourish and produce more gas, lactate, and total VFA. Acetate was responsible for the increase in total VFA, as no additional propionate or butyrate was observed.

Data in Table 1 indicate that a combination of carvacrol, thymol, and pinene, at both concentrations evaluated, 5 mM or 6.7 mM each of carvacrol and thymol, significantly reduced the number of viable anaerobic bacteria in the waste within 2 days, when compared with the control flasks. A complete bactericidal effect was not observed after 14 days, even at the higher concentration of carvacrol and thymol (6.7 mM); however, the number of organisms remain low similar to the 2-day population. The population of fecal coliforms was reduced to nondetectable levels after 4 days when carvacrol and thymol were combined at 6.7 mM each (Table 1). The absence of fecal coliforms in the control flasks after 14 days was likely due to acidification, as pH dropped to 4.2 after 14 days (FIG. 1C).

EXAMPLE 2

The Effect of the Antimicrobial Plant Oils on Cattle Waste under Natural Semi-Oxic Conditions (Lagoon/Basin Simulation).

Waste was collected and processed as in Example 1. The waste slurry was divided into 1-liter aliquots and poured into wide-mouth (10 cm) jars (17 cm tall, 13.5 cm diameter, 1.6-liters). The plant oils (carvacrol, thymol and α-pinene) were added to the slurry without stirring or mixing. Plastic lids provided with the jars were used to cover approximately 90% of the jar opening to prevent moisture loss over the 56-day experimental period. A wide mouth pipette was inserted into the slurry from top to bottom at which time slurry contents were simultaneously withdrawn. Total VFA production and butyrate production were measured as described in Example 1. The results are reported in FIGS. 2A and 2B.

Figure 2A:
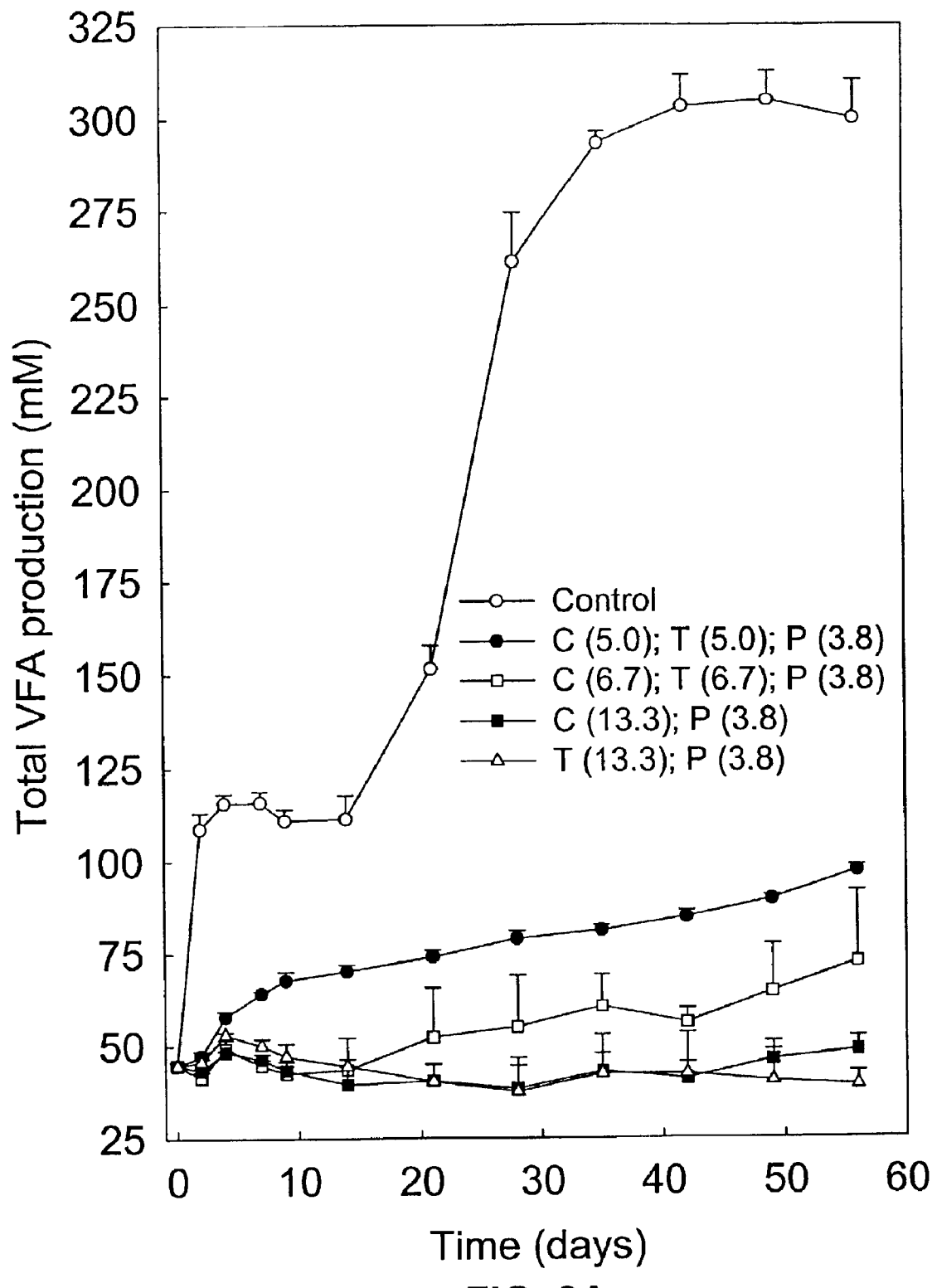
FIG. 2A is a graph showing the effect of various concentrations of carvacrol (C), thymol (T), and α-pinene (P) on total volatile fatty acid production of stored cattle waste in open wide-mouthed jars.
Figure 2B:
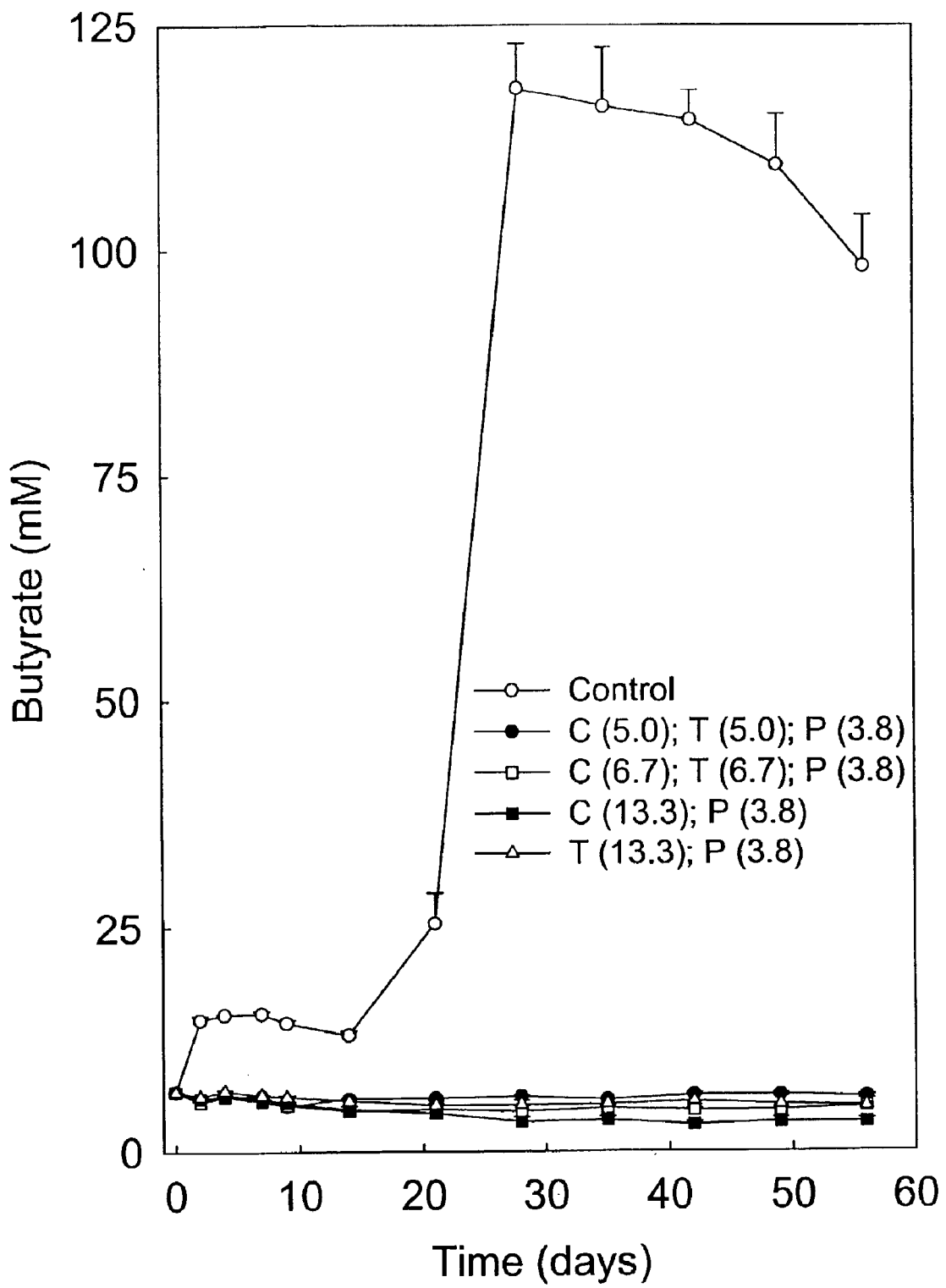
FIG. 2B is a graph showing the effect of various concentrations of carvacrol (C), thymol (T), and α-pinene (P) on butyrate production of stored cattle waste in open wide-mouthed jars.

The data in FIG. 2A indicate that carvacrol or thymol individually at 13.3 mM inhibited the production of short-chain volatile fatty acids equally or slightly better than the combination of the two oils (6.7 mM each) for 56 days. The control treatment exhibited a biphasic production of acids. There was an initial rapid production of acids up to day 4, and then another increase in acids beginning at day 14. In the control jars a crust began to form on top of the waste, which may have contributed to the secondary fermentation. Although acetate (40 mM) and propionate (25 mM) were produced, the predominant acid produced during this secondary fermentation (day 14 to 42) was butyrate (100 mM; FIG. 2B). Significant gas bubbles were produced beginning at day 12 to 14, which raised the crust to the top of the jar. Because of the high concentration of butyrate, we believe that a significant amount of the gas that was produced was hydrogen, resulting from a classic Clostridium butyricum fermentation. The crust did not form on any of the treated wastes.

EXAMPLE 3

The Effect of the Antimicrobial Plant Oils on Swine Waste under Anoxic Conditions.

Swine waste was processed similarly to the method described in Example 1. Fecal waste was randomly collected within 15 min of being excreted from animals fed a finishing diet of 85% corn and 11% soybean meal. Swine urine was collected from catheterized animals. Feces, urine, and distilled water in the ratio 50:35:15 were blended (Waring Inc., New Hartford, Conn.) for 1 min. Four replicate samples were obtained from this slurry and analyzed for various parameters and were considered as time 0. The waste slurry was divided into 500 ml aliquots and antimicrobial plant oils were added directly at the desired concentration, with one exception, in which carvacrol was dissolved 1:1 v:v in 95% ethanol, or 2 ml carvacrol/ethanol addition in these 500 ml slurries. The slurry was blended 1 min to provide a homogenous mixing of the antimicrobial oils and poured into 1-liter Erlenmeyer flasks, which were gassed with nitrogen (also after each sampling), sealed with a rubber stopper and left stationary at ambient temperature (25° C.). Treatments were in duplicate, and the contents of the flasks were gently swirled before being sampled at the days indicated in FIGS. 3–5. Gas volume and composition were analyzed in these flasks (anoxic slurry).

Methods of Analysis.

Head space gas was measured by displacement of a water-lubricated glass piston in a 50 ml syringe [Miller, T. L. et al. (1974), Appl Environ 27:985–987]. A 20-gauge needle with a Leurlok was inserted through the stopper, and a three-way valve was attached to the needle to allow gas volume to be periodically determined. Methane and hydrogen were analyzed as previously described [Varel, V. H. et al. (2000), *Curr Microbiol* 40:392–397].

A 15-ml waste sample was collected from each flask. The sample was mixed with 15 ml of 0.5 M $H_2SO_4$, centrifuged at 2000×g for 20 min at 4° C., and stored at −20° C. until analyzed [Varel, V. H. et al. (1999), *J Anim Sci* 77:1162–1168]. L-Lactate concentrations were determined with a membrane-immobilized system involving lactate oxidase (Model 27, Yellow Springs Instrument Co., Yellow Springs, Ohio, USA). Short-chain volatile fatty acids (VFAs; acetate, propionate, butyrate, valerate, isobutyrate, isovalerate) and aromatic compounds (cresol, indole, skatole, 4-ethylphenol, phenol) were determined in an aliquot from the original acidified sample. After thawing, the sample was centrifuged at 5° C., 10,000×g for 5 min. A 0.5 ml aliquot of the supernatant was combined with an internal standard, ethyl butyrate (0.25 mM final concentration), the sample was acidified with 0.4 ml of 3 M HC1, 0.8 ml ethyl ether was added, the sample was shaken vigorously for 1 min, and centrifuged at 5° C., 16,000×g for 1 min, and the ether phase was analyzed. To determine carvacrol and thymol concentrations, an aliquot of the original acidified sample which was not centrifuged, was treated as indicated above and extracted with ether twice. These two agents were found to primarily reside in the waste solids. Aromatic, VFAs, thymol and carvacrol were analyzed with a Hewlett Packard 6890 gas chromatograph equipped with a flame ionization detector and a Hewlett Packard 5973 mass selective detector. Compounds were separated on a 30 m×0.32 mm diameter (0.5 μm film thickness) Innowax PEG column using the following program parameters: flow rate was 1.9 ml $min^{-1}$, initial temperature was 140° C., initial time was 3 min with a temperature ramp of 7.5° C. $min^{-1}$, with a final temperature of 230° C. for 4 min. Injector and detector temperatures were 250° C. Data were analyzed as a split-plot in time with the GLM procedure of (SAS).

Figure 4A:
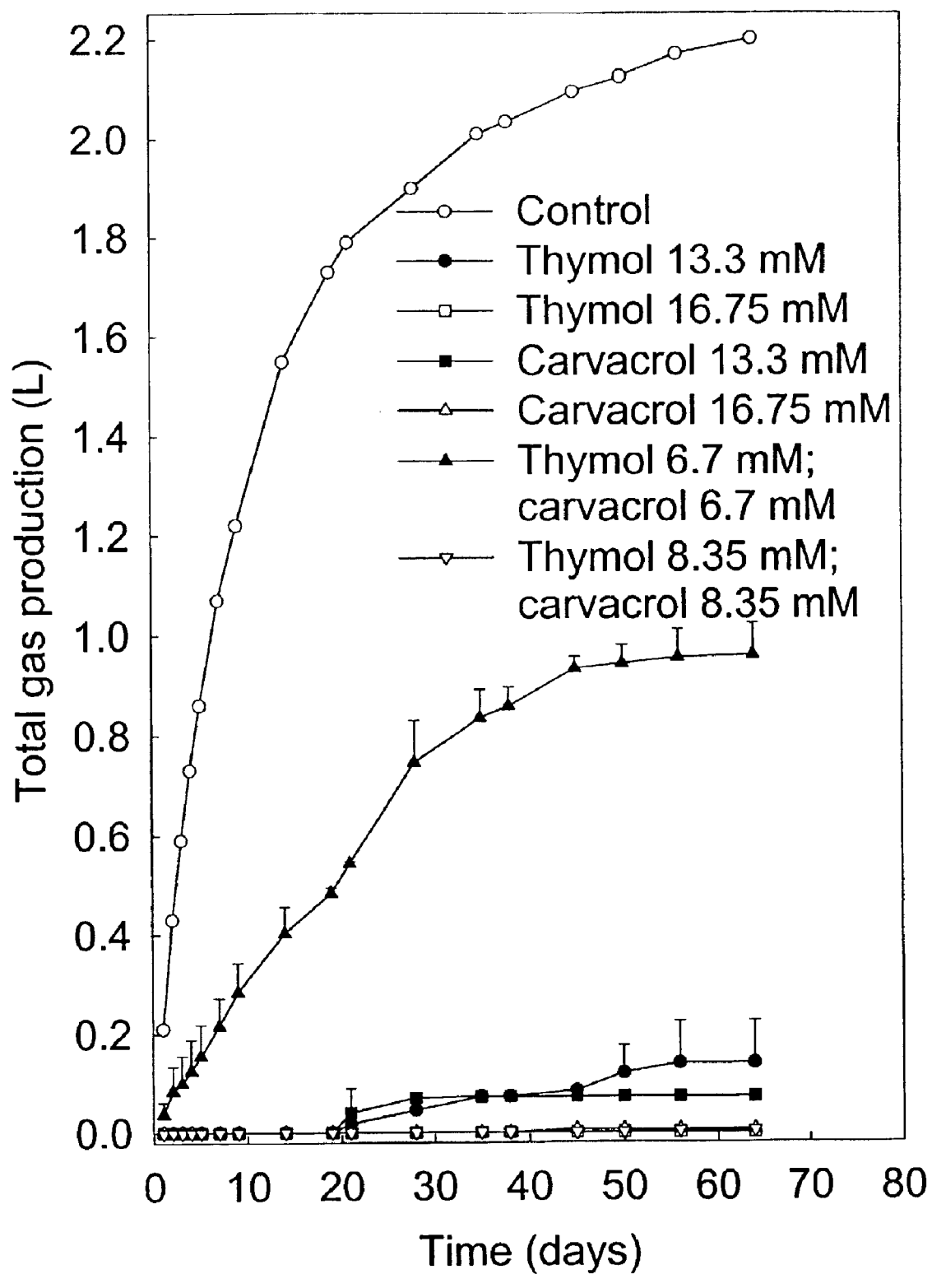
FIGS. 4A–4D are graphs showing the effects of thymol and carvacrol treatments on gas production (4A), VFAs (4B), L-lactate (4C), and pH (4D) in stored swine waste.
Figure 4B:
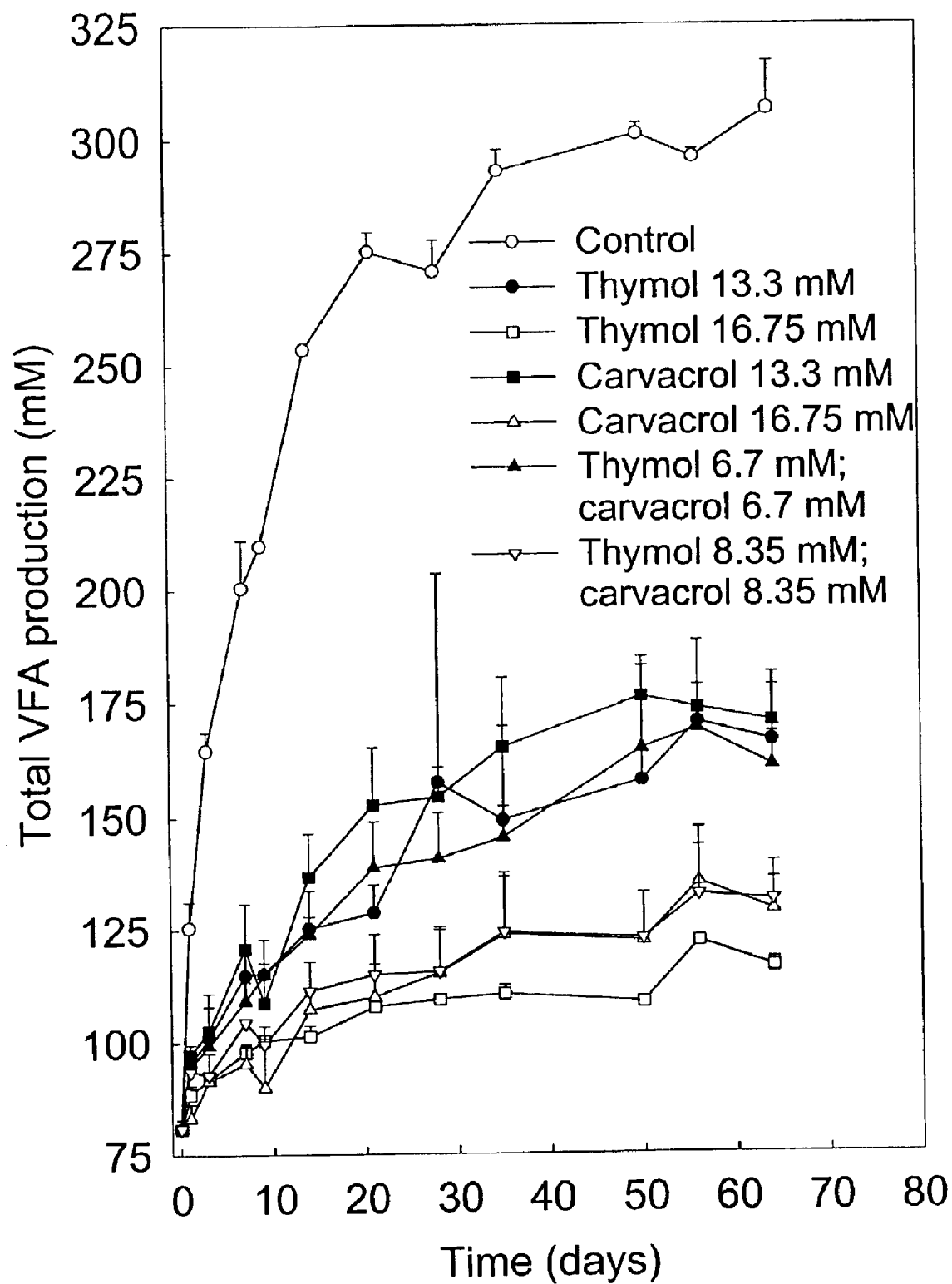
Figure 4C:
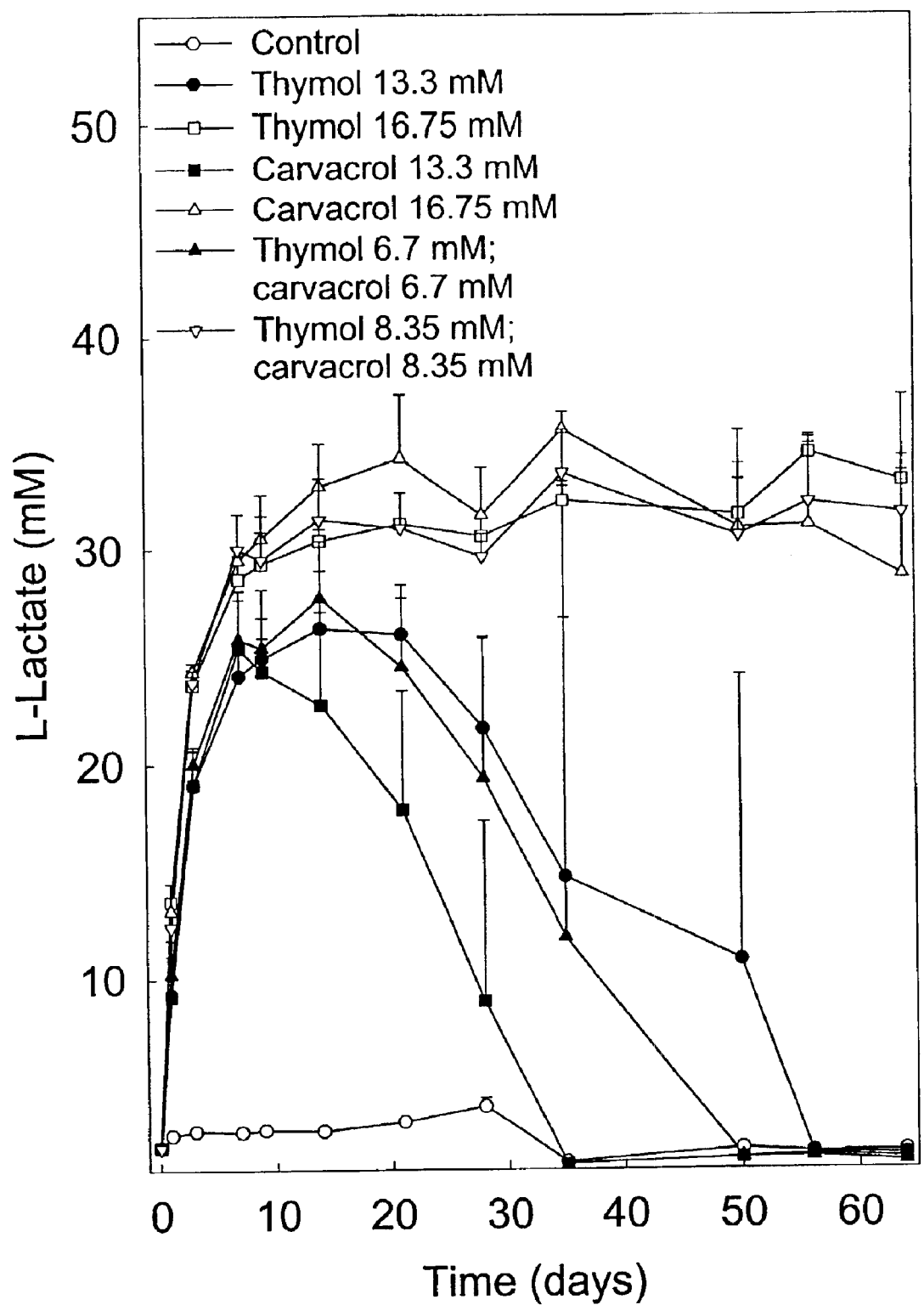
Figure 4D:
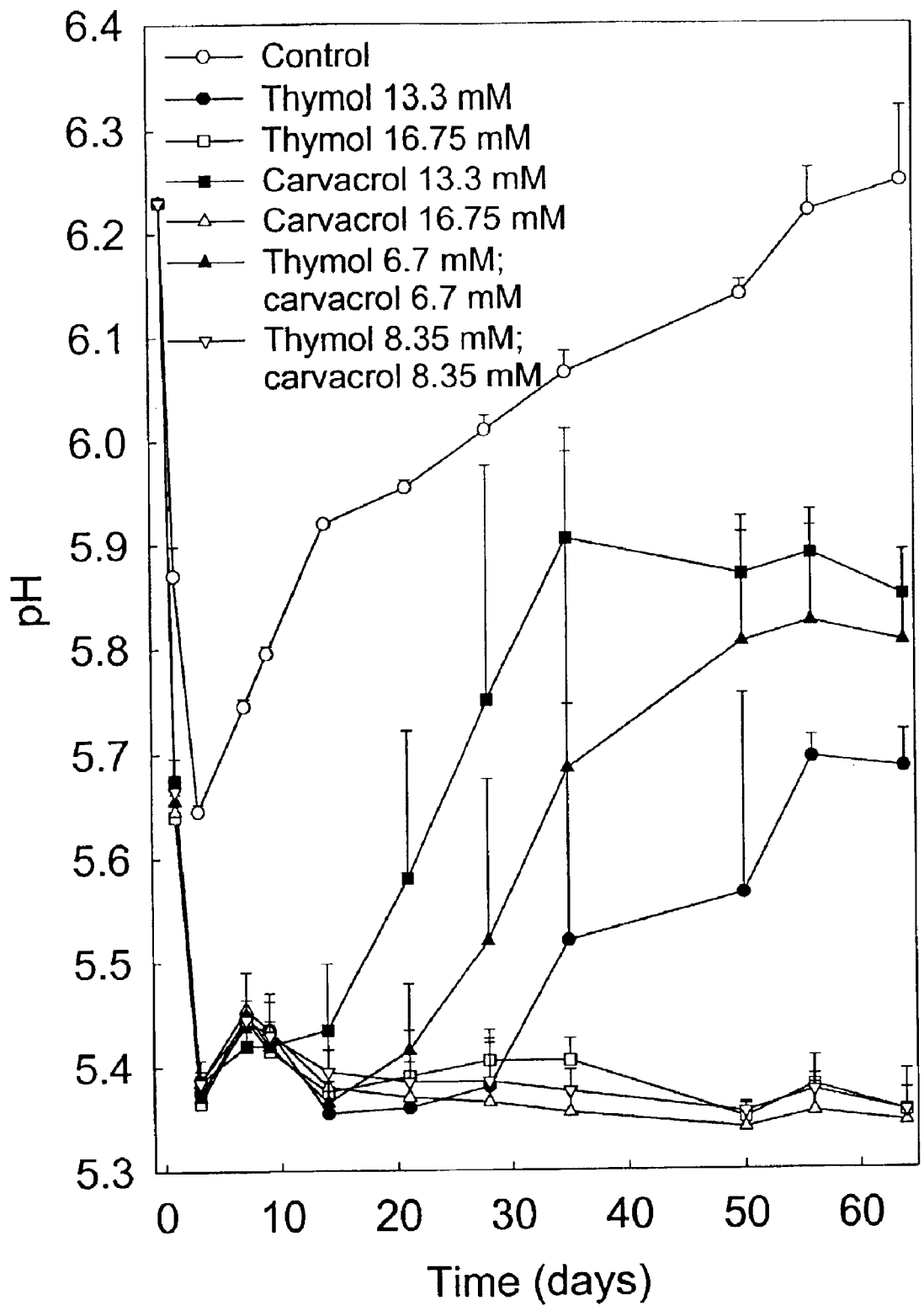

Carvacrol and thymol at 13.3 or 16.75 mM, or a combination of each to equal 16.75 mM, essentially stopped most gas production (FIG. 4A) and prevented any production of the offensive odor compounds valerate, isovalerate, isobutyrate and cresol (data not shown). Also, production of propionate was inhibited and only a minimum of butyrate (<8 mM) was produced in these treatments (data not shown). Acetate was the predominant acid that increased and was responsible for the increase in total VFA production (FIG. 4B). The gas composition (data not shown) from the control and combination thymol/carvacrol treatments (13.3 mM) was primarily methane, with traces of hydrogen (carbon dioxide was not measured). Trace amounts of methane were also detected after 20 days in the carvacrol and thymol treatments (13.3 mM). Lactate accumulated only when carvacrol or thymol were added to the waste; however, lactate decreased between day 10 and 20 in the 13.3 mM treatments (FIG. 4C). The pH decreased in the control and all treatments during the first 2 days (FIG. 4D); however, with the exception of the 16.75 mM carvacrol, thymol, and combination thymol/carvacrol treatments, pH rose with time which corresponded to the initiation of methane production and the disappearance of lactate (FIG. 4C).

Figure 5A:
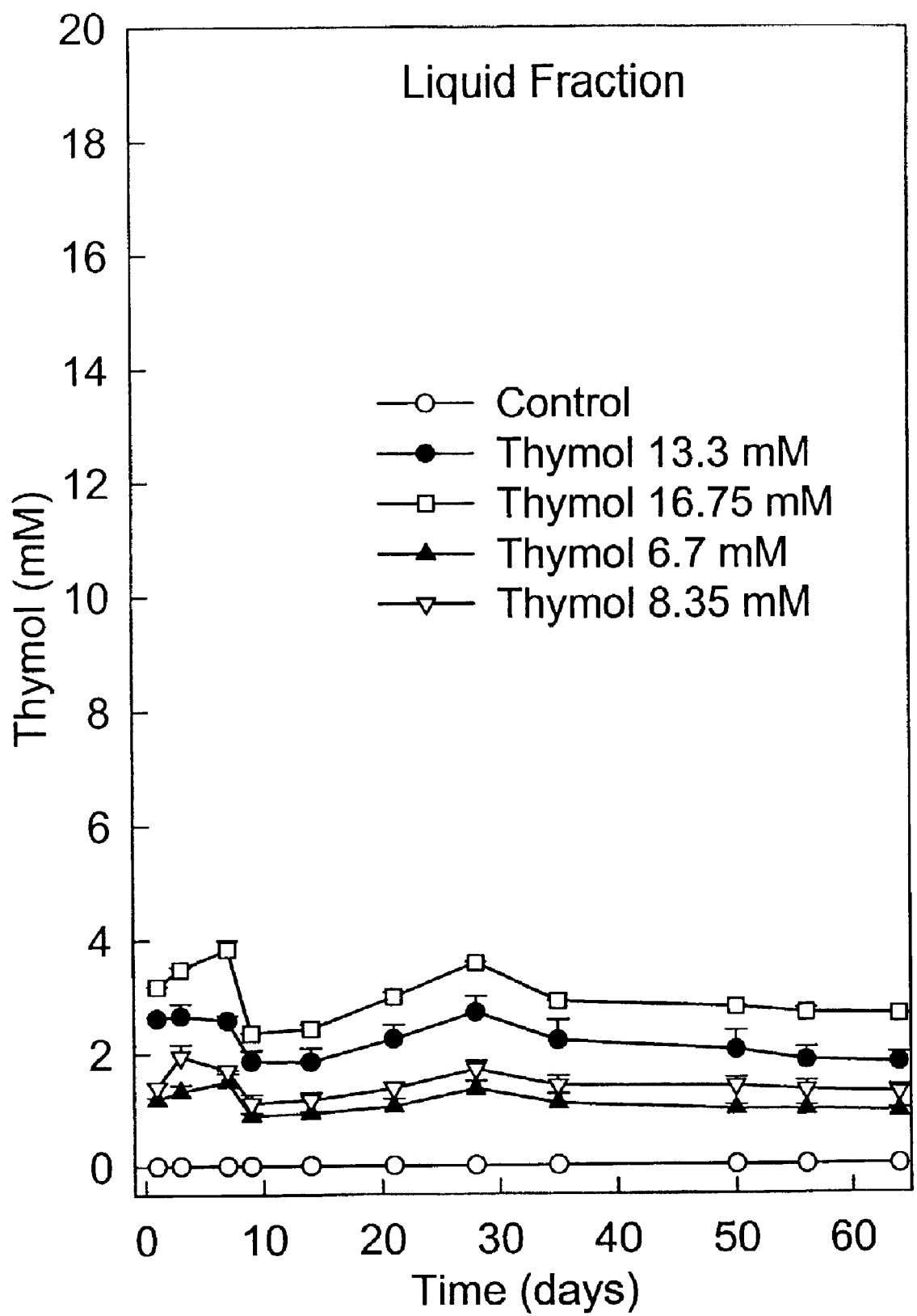
FIGS. 5A and 5B are graphs showing the recovery of thymol from the liquid and solid fractions of stored swine waste treated with thymol and carvacrol.
Figure 5B:
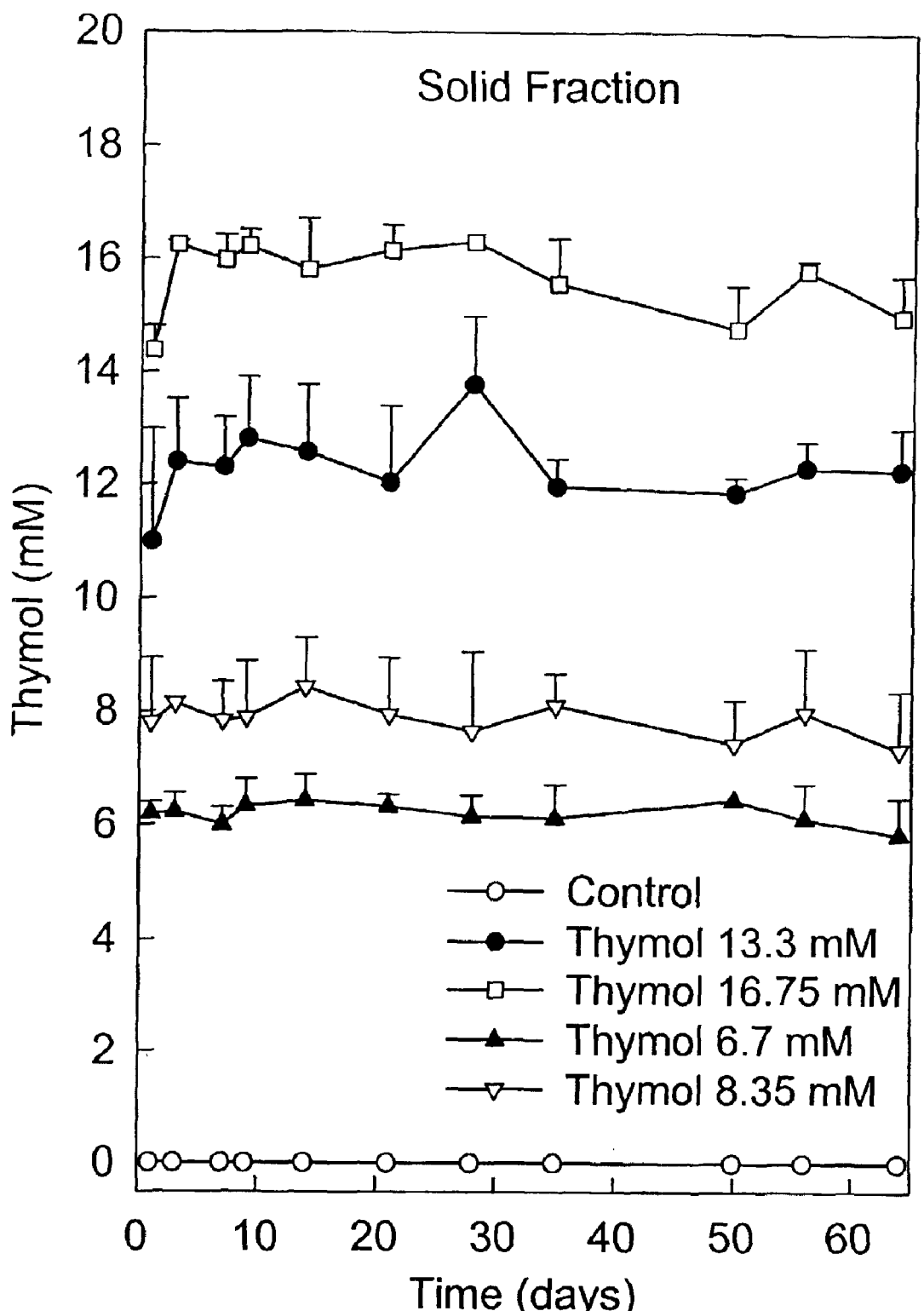

In general, less than 25% of the added thymol was recovered from the liquid or supernatant fraction of swine waste (FIG. 5A). However, from the solid fraction of the waste, 90 to 95% of the added thymol was recovered (FIG. 5B). The recoveries were similar for carvacrol from sealed flasks.

EXAMPLE 4

The Effect of the Antimicrobial Plant Oils on Swine Waste under Natural Semi-Oxic Conditions (Lagoon/Basin Simulation).

Swine waste was collected and processed into a slurry as in Example 3. As in Example 2, the slurry was added to wide-mouth (10 cm) jars (17 cm tall, 13.5 cm in diameter, 1.6-liter volume) with the test antimicrobial additives, and plastic lids were placed to cover approximately 90% of the jar opening to prevent moisture loss over the experimental period. The sampling procedure was similar to that described above in Example 3, except no stirring or mixing occurred before the contents were sampled, and treatments were in triplicate.

Total culturable anaerobic bacteria and fecal coliforms were enumerated from a 1-ml sample removed from the jars containing the control, 13.3 mM, and 20 mM carvacrol treatments as previously described [Varel, V. H. et al. (2001) *Appl Environ Microbiol* 67:1366–1370]. Fecal coliforms were enumerated with 3 M Petrifilm *Escherichia coli* coliform count plates (3 M Microbiology Products, St. Paul, Minn.). Both of the carvacrol treatments reduced (P<0.05) the number of viable anaerobic bacteria in the waste within 2 days when compared to the controls (Table 2). This effect was sustained for 28 days. The initial decrease in the concentrations of anaerobic bacteria from day 0 to 2 in the control is presumably because VFAs increase in this batch system and become lethal to a select population of organisms. No fecal coliforms were detected after 2 days when 20 mM carvacrol was added to the waste (Table 3). The 13.3 mM carvacrol treatment reduced (P<0.01) the fecal coliforms within 2 days, and none were detected at 14 days.

Figure 3:
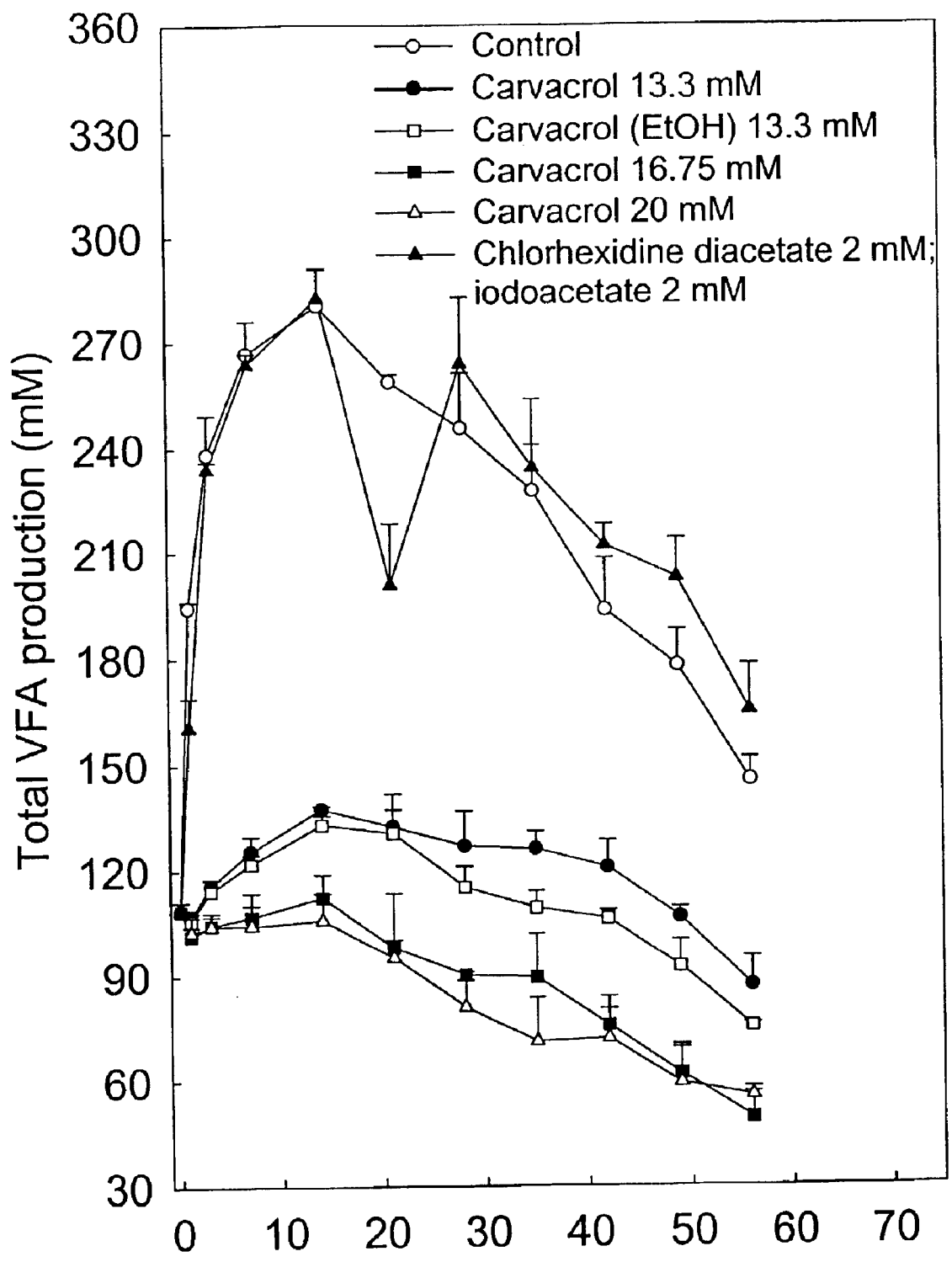
FIG. 3 is a graph showing the effects of various antimicrobial treatments on the production of total short-chain volatile fatty acids (VFAs) from stored swine waste.

The data in FIG. 3 indicate that a combination of chlorhexidine diacetate (2 mM) and iodoacetate (2 mM) had no inhibitory effect on the production of VFAs from swine waste in open jars when compared to control values. However, the three concentrations of carvacrol inhibited the production of VFAs (P<0.01). Dissolving carvacrol in ethanol prior to adding it to the waste had no effect (P>0.05) on its ability to inhibit VFA production; thus, it was not dissolved in subsequent experiments.

Carvacrol and thymol were both recovered from open jars after 56 days at 90 to 95% of added concentrations, indicating that these aromatic chemicals did not volatilize from open vessels (data not shown).

EXAMPLE 5

The Affect of Eugenol and Thymol on Cattle Waste under Anoxic Conditions.

Figure 6A:
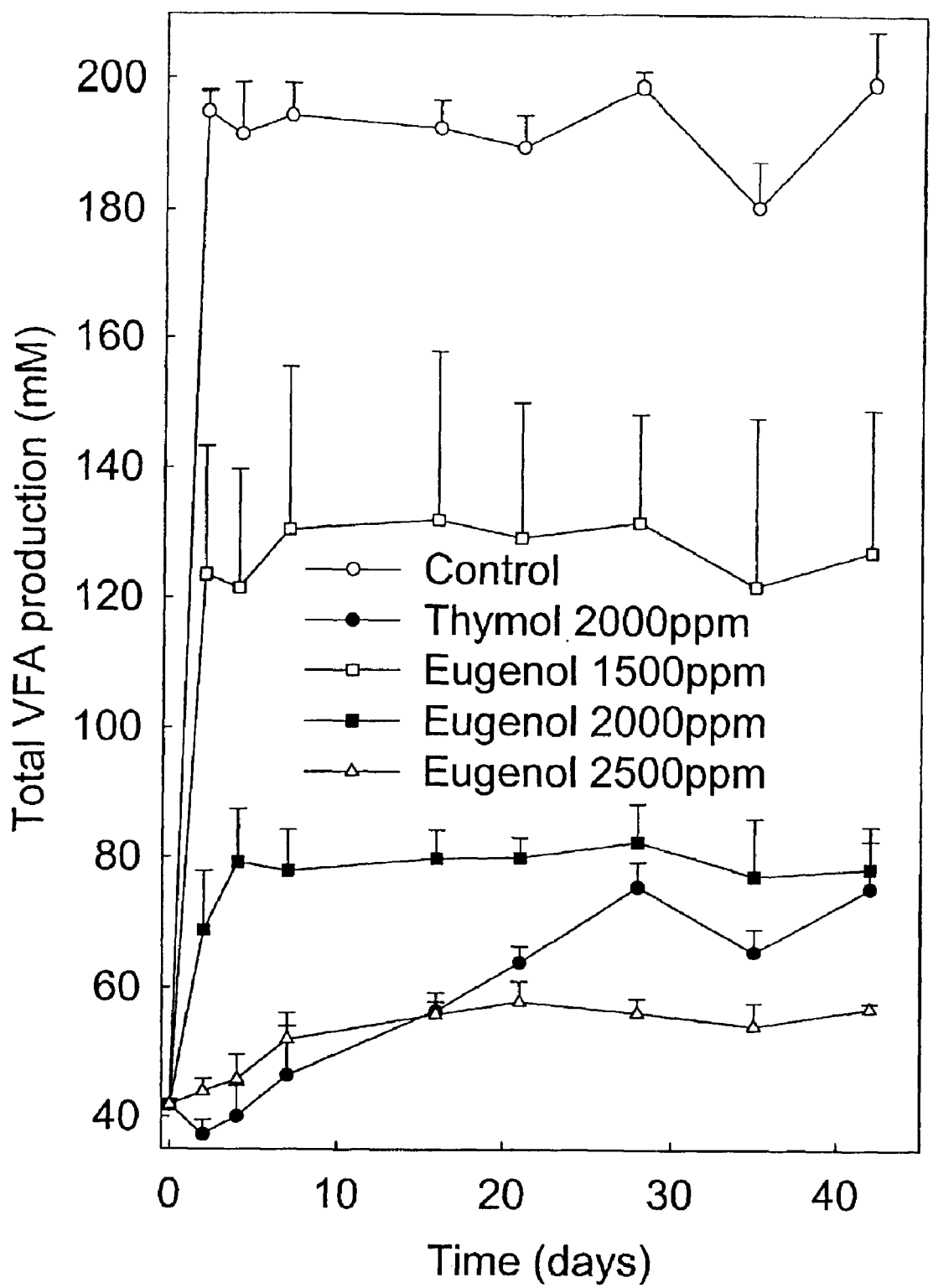
FIGS. 6A and 6B are graphs showing a comparison of thymol with various concentrations of eugenol on the production of VFAs (6A) and L-lactate (6B) from stored cattle waste in anoxic flasks.
Figure 6B:
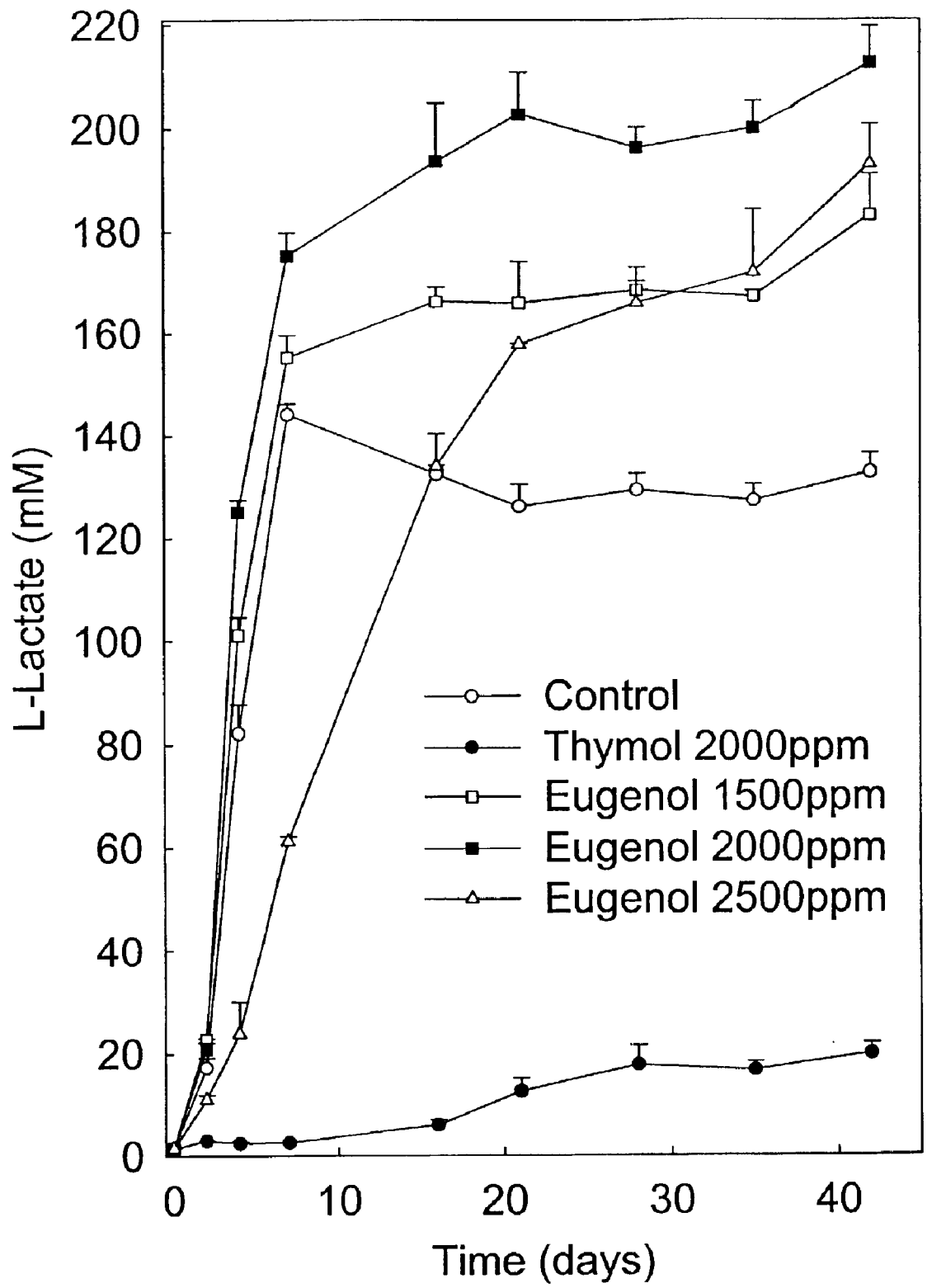

Waste was collected and processed as in Example 1. The waste slurry was divided into 500-ml aliquots and eugenol or thymol were added directly at the desired concentration. The slurry was blended 1 min to provide a homogeneous mixing of the antimicrobial oils and poured into a 1-liter Erlenmeyer flask, which was sealed with a rubber stopper and left stationary at ambient temperature (25° C.). Treatments were in triplicate, and the contents of the flask were gently swirled before being sampled at the times indicated. Short-chain volatile fatty acids and L-lactate in the flasks were determined as described in Example 1. These results are reported in FIGS. 6A and 6B. Data in FIG. 6A indicate that eugenol at 2000 or 2500 ppm (13.3 or 16 mM) is equally or more effective over a 42-day period in controlling the production of total VFA from cattle waste when compared to 2000 ppm (13.3 mM) thymol. The data indicate inhibition of VFA production by eugenol is concentration dependent. Previous results and data in FIG. 6B indicate that thymol inhibits production of L-lactate. Contrary to those results, the data in FIG. 6B indicate that eugenol, at all concentrations evaluated, stimulates L-lactate production in cattle waste. This is a desirable effect in some cases because it rapidly lowers the pH which contributes to inhibiting the overall fermentation of the wastes, and more ammonia nitrogen will be retained in the wastes.

I claim:

1. A method for inhibiting fermentative production of gaseous emissions, production of short chain volatile fatty acids and the viability of total anaerobic bacteria and fecal coliforms, and for promoting lactic acid accumulation in waste selected from the group consisting of excreta, feedlot waste and mixtures thereof, comprising applying to said waste an agent comprising eugenol and a component selected from the group consisting of carvacrol, thymol, and a mixture thereof in an amount effective to provide said inhibiting of fermentative production of gaseous emissions, production of short chain volatile fatty acids and the viability of total anaerobic bacteria and fecal coliforms, and promoting of lactic acid accumulation.

2. The method of claim 1, wherein said waste is excreta of an animal.

3. The method of claim 1, wherein said excreta is urine or fecal material.

4. The method of claim 1, wherein said waste is human excreta.

5. The method of claim 2, wherein said animal is a herbivore.

6. The method of claim 2, wherein said animal is selected from the group consisting of cattle, swine, sheep, bison, horses, poultry, and exotic animals.

7. The method of claim 1, wherein said waste is accumulated waste present in a pit toilet, portable toilet, manure treatment lagoon, or in an animal confinement area.

8. The method of claim 1, wherein said agent is comprised of less than 50% eugenol.

9. The method of claim 1, wherein said agent is applied to said waste at a concentration of at least 10 mM.

10. The method of claim 1, wherein said agent is applied to said waste at a concentration of at least 13 mM.

11. The method of claim 1, wherein said agent is applied to said waste at a concentration of at least 16 mM.

12. A composition comprising waste selected from the group consisting of excreta, feedlot waste, and mixtures thereof and an agent comprising eugenol and a component selected from the group consisting of carvacrol, thymol, and mixture thereof, said composition produced as a result of the method of claim 1.

13. The composition of claim 12, wherein said waste is excreta of an animal.

14. The composition of claim 12, wherein said excreta is urine or fecal material.

15. The composition of claim 12, wherein said waste is human excreta.

16. The composition of claim 13, wherein said animal is a herbivore.

17. The composition of claim 13, wherein said animal is selected from the group consisting of cattle, swine, sheep, bison, horses, poultry, and exotic animals.

18. The composition of claim 12, wherein said agent is applied to said waste at a concentration of at least 10 mM.

19. The composition of claim 12, wherein said agent is applied to said waste at a concentration of at least 13 mM.

20. The composition of claim 12, wherein said agent is applied to said waste at a concentration of at least 16 mM.

* * * * *